(12) United States Patent
Chen et al.

(10) Patent No.: US 11,253,556 B2
(45) Date of Patent: Feb. 22, 2022

(54) LACTOBACILLUS FERMENTUM GKF3, COMPOSITION COMPRISING THE STRAIN AND METHOD FOR IMPROVING PSYCHATAXIA USING THE SAME

(71) Applicant: GRAPE KING BIO LTD, Taoyuan (TW)

(72) Inventors: Chin-Chu Chen, Taoyuan (TW); Yen-Lien Chen, Taoyuan (TW); Shih-Wei Lin, Taoyuan (TW); Szu-Yin Wu, Taoyuan (TW); Yen-Po Chen, Taoyuan (TW); Yu-Hsin Hou, Taoyuan (TW); Ci-Sian Wang, Taoyuan (TW); Yang-Tzu Shih, Taoyuan (TW); Jia-Lin Jiang, Taoyuan (TW)

(73) Assignee: GRAPE KING BIO LTD, Taoyuan (TW)

( * ) Notice: Subject to any disclaimer, the term of this patent is extended or adjusted under 35 U.S.C. 154(b) by 113 days.

(21) Appl. No.: 16/675,667

(22) Filed: Nov. 6, 2019

(65) Prior Publication Data

US 2020/0155623 A1    May 21, 2020

(30) Foreign Application Priority Data

Nov. 21, 2018 (TW) .................................. 107141359

(51) Int. Cl.
| | | |
|---|---|---|
| *A61K 35/747* | (2015.01) | |
| *A61K 35/00* | (2006.01) | |
| *A61K 39/09* | (2006.01) | |
| *A23L 29/00* | (2016.01) | |

(52) U.S. Cl.
CPC .......... *A61K 35/747* (2013.01); *A23L 29/065* (2016.08); *A61K 39/09* (2013.01); *A61K 2035/115* (2013.01)

(58) Field of Classification Search
None
See application file for complete search history.

(56) References Cited

U.S. PATENT DOCUMENTS

| | | |
|---|---|---|
| 2008/0299098 A1 | 12/2008 | Se et al. |
| 2020/0155623 A1 | 5/2020 | Chen et al. |
| 2020/0237834 A1 | 7/2020 | Mulder et al. |

FOREIGN PATENT DOCUMENTS

| | | |
|---|---|---|
| CA | 3033032 | 2/2018 |
| JP | H01191684 A | 8/1989 |
| JP | H0923848 A | 1/1997 |
| JP | 2015213501 A | 12/2015 |
| JP | 2020-080861 A | 6/2020 |
| TW | 201825670 A | 7/2018 |
| TW | I715177 B | 1/2021 |

OTHER PUBLICATIONS

Foster et al "Gut-Brain Axis: How the Microbiome Influences Anxiety and Depression", Trends in Neurosciences, vol. 36, No. 5, p. 305-312, May 2013.
S. Liang et al "Administration of *Lactobacillum helveticus* NS8 Improves Behavioral, Cognitive, and Biochemical Aberrations Caused by Chronic Restraint Stress", Neuroscience, vol. 310, p. 561-577, Dec. 3, 2015.
Yen-Wenn Liu et al "Psychotropic Effects of *Lactobacillum plantarum* PS128 in Early Life-Stressed and Naive Adult Mice", Brain Research, vol. 1631, p. 1-12, Jan. 15, 2016.
Chang et al., "Probiotic characteristics of lactic acid bacteria isolated from kimchi", Journal of Applied Microbiology, vol. 109, Issue 1, Jul. 2010, 11 pages.
Wang et al., "*Lactobacillus fermentum* NS9 restores the antibiotic induced physiological and psychological abnormalities in rats", Beneficial Microbes, Wageningen Academic Publishers, 2015, vol. 6, Issue 5, pp. 707-717, 11 pages.
Hadizadeh et al., "Probiotic supplementation improves the cognitive function and the anxiety-like behaviors in the stressed rats", Iranian Journal of Basic Medical Sciences, 2019, vol. 22, Issue 5, pp. 506-514, 9 pages.
Dao Dong Pan et al., "Characterisation of *Lactobacillus fermentum* SM-7 isolated from koumiss, a potential probiotic bacterium with cholesterol-lowering effects", Society of Chemical Industry, Wiley Online Library, vol. 91, Oct. 28, 2010, 7 pages.
Gao Dongping, A study of the relationship between depression and intestinal flora based on bibliometrics, Article, 2017, 173-176, vol. 14, No. 14, China Medical Herald.

*Primary Examiner* — Sarvamangala Devi
(74) *Attorney, Agent, or Firm* — Hayes Soloway P.C.

(57) ABSTRACT

The present invention provides a *Lactobacillus fermentum* GKF3, a composition comprising the strain and their use, in which the aforementioned *Lactobacillus fermentum* GKF3, deposited with accession numbers of BCRC 910824 and CGMCC 15203, can increase the levels of dopamine or/and serotonin in brain tissues, thereby improving the symptoms of the psychataxia such as decreased focus.

4 Claims, 6 Drawing Sheets
Specification includes a Sequence Listing.

LACTOBACILLUS FERMENTUM GKF3, COMPOSITION COMPRISING THE STRAIN AND METHOD FOR IMPROVING PSYCHATAXIA USING THE SAME

RELATED APPLICATION

This application claims priority to an earlier Taiwan Application Serial Number 107141359, filed Nov. 21, 2018, which is incorporated herein by reference in its entirety.

BACKGROUND

Field of Invention

The present invention relates to a lactic acid bacterium for improving psychataxia, a composition containing the strain and the method for improving psychataxia using the same. More particularly, the present invention relates to a composition containing *Lactobacillus fermentum*, in which the composition increases the dopamine and/or serotonin levels in the brain tissues to improve psychataxia when given to a subject.

Description of Related Art

Psychataxia

Modern people have a lot of course or work stresses which make more and more people have anxiety problems and develop symptoms such as insomnia, dysautonomia, etc., resulting in decreased focuses. More seriously, depression may occur.

Dopamine

Dopamine is a brain neurotransmitter for stimulating motivation and drive as well as assisting neurons in sending pulses. Moreover, dopamine is a neurotransmitter responsible for lust as well as the transmission of exciting and happy signals. Dopamine also relates to addiction. With the function of sending happy and exciting emotions, dopamine has been used to treat depression medically.

Dopamine disorders or deficiencies lead to a lack of motivation, a loss of energy, inattention or a loss of the ability to control muscles. A serious dopamine deficiency may cause involuntary tremor of limbs and even evolve into Parkinson's disease. However, the oversecretion of dopamine may cause excessive physical exertion and energy, thereby resulting in death.

Serotonin

Serotonin, or called 5-hydroxytryptamine, abbreviated as 5-HT, is a monoamine neurotransmitter. Serotonin is mainly stored in animal gastrointestinal tracts, blood platelets and central nervous systems, in which 2% of total serotonin is in the brain, while 90% are located in the enterochromaffin cells and the intermuscular plexus, where it participates in the regulation of intestinal movements. Serotonin is generally believed to be a contributor to feelings of well-being and happiness since serotonin regulates people's emotions, feelings of stress and concentration as well as contributes mental stability and serenity to people. A worker having a low serotonin level feels anxious and unsafe easily, resulting in the decline of working efficiency.

There are many reasons for a serotonin decrease, including stress, a lack of sleep, nutritional deficiency and a lack of training, etc. If the serotonin level is lower than the necessary amount, problems like having difficulties to pay attention, etc., may occur, thereby indirectly affecting individual abilities to plan and organize, often followed by stress and tiredness. Further decrease in serotonin levels may cause depression. Other symptoms related to the decreased brain serotonin level include irritability, anxiety, tiredness, chronic pain and restless, etc. The deterioration of the symptoms may finally cause diseases like obsessive-compulsive disorder, chronic fatigue syndrome, arthritis, fibromyalgia, hypomania, and depression, etc.

*Lactobacillus fermentum*

*Lactobacillus fermentum*, often found in the fermented animal or plant material, is a gram-positive species in the genus *Lactobacillus* that is first found in the sourdough. Lately, some strains have been used to treat women genitourinary system infections.

Application of *Lactobacillus* spp.

Recently, few reports have shown that intestinal microorganisms may affect human brain development, behaviors and emotions. One report has discovered that intestinal microorganisms can influence mice's emotions via the gut-brain axis, resulting in anxiety-like or depression-like symptoms (Foster and McVey Neufeld, 2013). Another report has also shown that the anxiety-like and depression-like behaviors of mice, resulted from the maternal separation, could decrease after the mice being administered with *Lactobacillus plantarum*, as indicated by the significant decrease of the immobile time during the forced swimming test and increased preference for sucrose. This result also shows that the *Lactobacillus plantarum* is helpful to improve the depression-like behaviors of mice by increasing the total amount of dopamine in the prefrontal cortex of a mouse and decreasing the serotonin metabolism rate (Liu et al., 2016). The other report has also found that after the rats were restraint for 21 days to induce the behavior of depression and anxiety, the anxiety and depression problems of the rats can be improved by administering *Lactobacillus helveticus* (Liang et al., 2015). However, the current market still requires the development of other strains to improve psychataxia-related diseases.

SUMMARY

The invention provides a bacterial strain, *Lactobacillus fermentum* GKF3, which is deposited in Bioresource Collection and Research Center (BCRC), Food Industry Research and Development Institute, Hsinchu 30062, Taiwan, on February, 12, 2018, and in China General Microbiological Culture Collection Center (CGMCC), Chinese Academy of Sciences, Beijing 100101, People's Republic of China, on Jan. 12, 2018 with an accession number of BCRC 910824 and CGMCC 15203, respectively.

Preferably, the *Lactobacillus fermentum* GKF3 has an acid tolerance, a bile salt tolerance and/or a heat tolerance.

The invention also provides a composition comprising *Lactobacillus fermentum* GKF3, which has been deposited in Bioresource Collection and Research Center (BCRC), Food Industry Research and Development Institute, Hsinchu 30062, Taiwan, on Feb. 12, 2018, and in China General Microbiological Culture Collection Center (CGMCC), Chinese Academy of Sciences, Beijing 100101, People's Republic of China, on Jan. 12, 2018 with an accession number of BCRC 910824 and CGMCC 15203, respectively, to improve psychataxia.

Preferably, *Lactobacillus fermentum* GKF3 (BCRC 910824, i.e., CGMCC 15203) is prepared by the following steps:

(a) inoculating an isolated colony of the *Lactobacillus fermentum* GKF3 into a liquid medium to perform a liquid culture; and (b) performing a mass production of the step (b) to obtain a whole fermented liquid comprising *Lactobacillus fermentum* GKF3 and a fermented liquid.

Preferably, the *Lactobacillus fermentum* GKF3 is further prepared by the following steps:

(c) centrifuging the whole fermented liquid of step (b) to obtain a pellet; and (d) lyophilizing on the pellet of the step (c).

Preferably, the step (a) is performed at a temperature of 25 to 40° C., a ventilation of 0 to 1 volume per volume per minute (vvm) of $N_2$ or $CO_2$, a rotational speed of 250 to 1000 rounds per minutes (rpm), and/or an incubation period of 16 to 24 hours.

Preferably, the pellet of the step (c) is further mixed with a protecting agent before being lyophilized.

Preferably, the pellet in the step (d) is lyophilized first at 0° C. to –20° C. for 1 to 4 hours, –15° C. to –40° C. for the next 4 to 8 hours, and then frozen under –196° C. to –40° C. for more than 8 hours.

Preferably, the composition comprises at least one additive selected from the group consisting of an excipient, a preservative, a diluent, a filler, an absorbefacient, a sweetener and any combination thereof.

Preferably, the composition is a drug, a feed, a drink, a nutritional supplement, a dairy product, a geriatric food, a baby food, a non-staple food or health food.

Preferably, a form of the composition is a powder, a tablet, a pellet, a suppository, a microcapsule, an ampoule, a liquid or a spray.

The present invention has provided a method for improving psychataxia of a subject by administering a composition of *Lactobacillus fermentum* GKF3.

Preferably, the composition increases a dopamine release in a brain tissue of the subject.

Preferably, the composition increases a serotonin release in a brain tissue of the subject.

Preferably, the symptoms of the psychataxia comprise insomnia, dysautonomia, decreased focus, depression and any combination thereof that can be reduced after administering *Lactobacillus fermentum* GKF3.

BRIEF DESCRIPTION OF THE DRAWINGS

The invention can be more fully understood by reading the following detailed description of the embodiment, with reference made to the accompanying drawings as follows.

DETAILED DESCRIPTION

Origin of Strain

Figure 1:
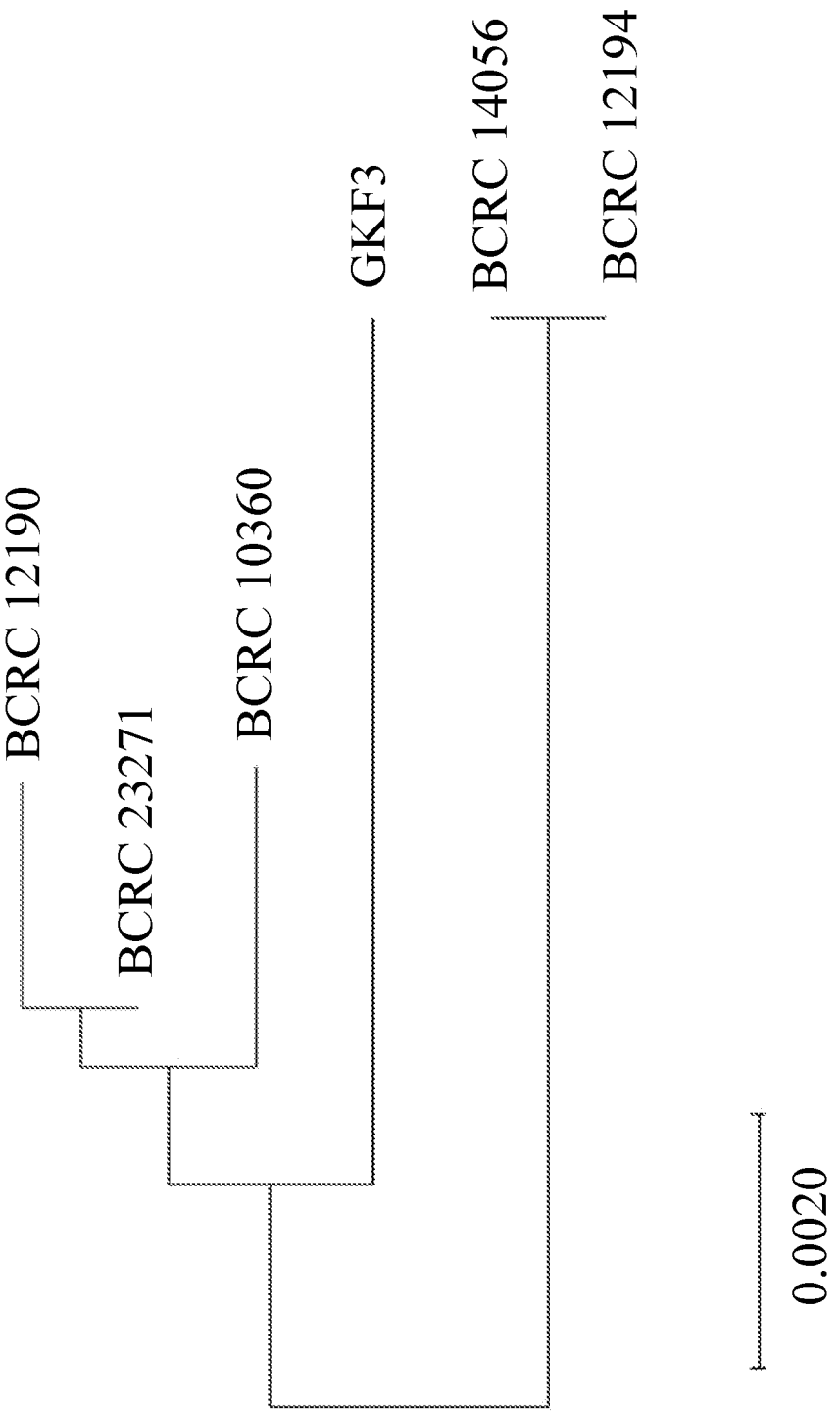
FIG. 1 is the phylogenetic tree of the recN gene of *Lactobacillus fermentum* GKF3 and other strains.

A strain of lactic acid bacteria (LAB) used in the experiment was *Lactobacillus fermentum* of the *Lactobacillus* genus. In a preferred embodiment, the species was collected from the traditionally pickled and fermented kimchi sold by a street vendor in Beipu Township, Hsinchu County 314, Taiwan. After collection, the samples of strains were sent to a laboratory for isolation.

Strain Screening and Culturing

Bags of the samples were placed in a laminar flow cabinet and were homogenized in ten times the weight of water by a blazer to obtain homogenized samples. Afterwards, 1 mL of each homogenized sample was transferred into De Man, Rogosa and Sharpe (MRS) medium containing 0.1% bromocresol green at 37° C. for 16 hours to increase populations of the *Lactobacillus fermentum* in the homogenized sample, as well as to increase other lactic acid bacteria (LAB) strains that were found in lower numbers. The homogenized samples were serially diluted after the enrichment culture, thereby obtaining diluted samples. After $10^5$-fold and $10^6$-fold serial dilution, 0.1 mL aliquots of each diluted sample were respectively transferred onto sterilized Petri dishes, each of which respectively contained culture media such as Rogosa agar, *Bifidobacterium lodoacetate* Medium 25 (BIM-25) agar, potato starch/yeast extract agar, bromocresol green MRS agar or bromocresol purple MRS agar. After an anaerobic incubation at 37° C. for 40 hours, 15 to 20 single colonies on each agar were isolated to be tested in the following biological assay. RAW 264.7 cells induced by lipopolysaccharide (LPS) was a classical cell model for inflammation research and could be an excellent platform for the investigation of the anti-inflammatory effect of lactic acid bacteria. After the screening test, the high-performance bacterial strains with greater than 80% inhibitory rate of NO and tumor necrosis factor α (TNF-α) in the cell model were first selected. Among these strains with high anti-inflammatory activities, strains with high activities of the tryptophan decarboxylase were further selected for subsequent experiments as they are precursors for the biosynthesis of serotonin.

Genotyping—Phylogenetic Tree

To study the uniqueness of strain *Lactobacillus fermentum* GKF3 (GKF3) in the evolution of species *L. fermentum*, the gene sequences of GKF3 and that of five strains of the *L. fermentum*, BCRC 10360, BCRC 12190, BCRC 12194, BCRC 14056 (same as ATCC 9338, ATCC 14931 and ATCC 11739 which were also deposited American Type Culture Collection, ATCC, Virginia Va. 20110, USA; both of BCRC 12194 and BCRC 14056 were ATCC 11739) and ATCC 23271, purchased from the Bioresource Collection and Research Center (BCRC), Food Industry Research and Development Institute, Hsinchu 30062, Taiwan or American Type Culture Collection (ATCC), Virginia Va. 20110, USA, were compared. Briefly, the GKF3 and the five purchased strains were cultured in mass production, followed by the extraction of the genome DNA (gDNA). Then, PCR was conducted with the primer pairs listed in TABLE 1 with the following conditions: 94° C. for 3 min, 35 cycles of 94° C. for 30 sec, 58° C. for 30 sec and 72° C. for 1 min 10 sec, and finally 72° C. for 5 min.

TABLE 1

Primer Pairs for recN in PCR

| Name | Sequences | Sequence identification numbers (SEQ ID NO) |
|---|---|---|
| Lf-recN-F | 5'- ATCCAAGGTCAAAATGAGCA -3' | SEQ ID NO: 01 |
| Lf-recN-R | 5'- CTTCAACCCGTTGGTTAGTG -3' | SEQ ID NO: 02 |

After the aforementioned reactions, DNA sequencing was performed to obtain recN gene sequences of GKF3 (SEQ ID NO: 03) and five purchased strains, followed by a recN gene phylogenetic tree constructed by a MEGA X software with a Neighbor-Joining mode. FIG. 1 was the phylogenetic tree of the recN gene of *Lactobacillus fermentum* GKF3 and other strains, in which the horizontal lines were branches representing evolutionary changes measured in a unit of genetic divergence, and the bar at the bottom was the scale of the branch lengths. Within the recN gene phylogenetic tree, GKF3 was a single branch itself separated from the other strains. The result indicated that in the view of genetic differences, the GKF3 was obviously different from known *Lactobacillus* spp. strains and was identified as a new *Lactobacillus* spp. strain. Therefore, the GKF3 was named as *Lactobacillus fermentum* GKF3 and deposited with the accession number of BCRC 910824 in Bioresource Collection and Research Center (BCRC), Food Industry Research and Development Institute, Hsinchu 30062, Taiwan, on Feb. 12, 2018, followed by a viability test on Mar. 1, 2018. The GKF3 was also deposited with an accession number of CGMCC 15203 in China General Microbiological Culture Collection Center (CGMCC), Chinese Academy of Sciences, Beijing 100101, People's Republic of China, on Jan. 12, 2018, followed by the viability test on the same day.

Phenotypic Analysis—Acid Tolerance Test

GKF3 and other four strains purchased from BCRC or ATCC, ATCC 23271, BCRC 12190, BCRC 12194 and BCRC 10360, were recovered. By adding HCl into original De Man, Rogosa and Sharpe (MRS) liquid media, a pH value of the original MRS liquid medium was adjusted from 6.5 to three different pH values: pH 3.2, pH 2.4 and pH 2.0. The strains were inoculated in the aforementioned MRS liquid media with different pH values and incubated at 37° C. for 3 hours, followed by serial dilution, spread plate, incubation and finally colony count. Experimental results were shown in TABLE 2 and FIG. 2.

Figure 2:
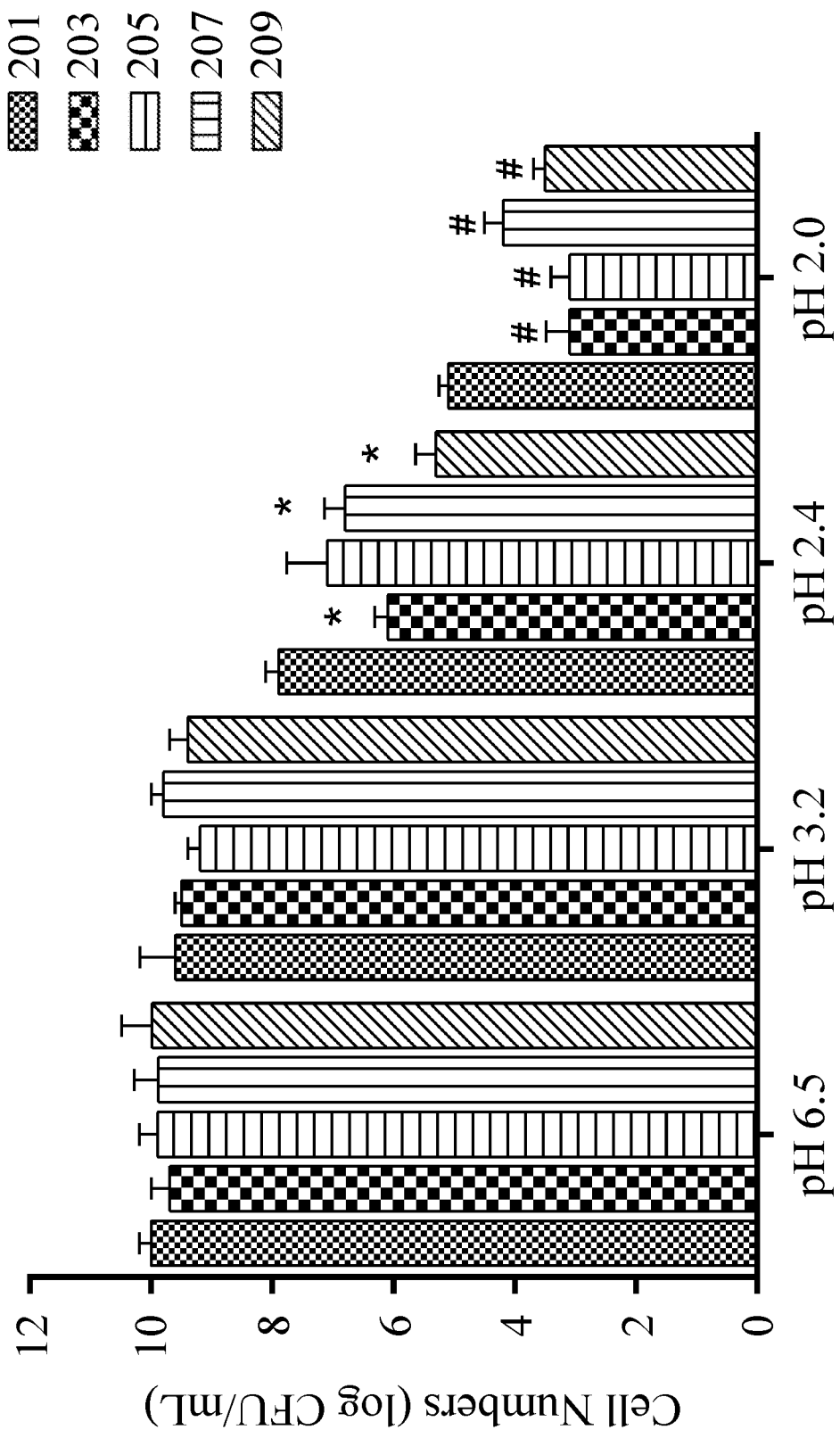
FIG. 2 shows the viable cell numbers of *Lactobacillus fermentum* GKF3 and other strains in the acid tolerance test.

FIG. 2 represented cell numbers of *L. fermentum* GKF3 and other strains in the acid tolerance test. The horizontal axis represented the pH values, and the vertical axis showed the cell numbers as log colony-forming units per milliliter (CFU)/mL. The bars 201, 203, 205, 207 and 209 represented the GKF3, ATCC 23271, BCRC 12190, BCRC 12194 and BCRC 10360, respectively. The symbols "*" and "#" represented significant differences in cell numbers between GKF3 and the other purchased strains at pH 2.4 and pH 2.0, respectively (p<0.05).

As shown in TABLE 2 and FIG. 2, the cell numbers of GKF3 (bar 201) and the other four strains (bars 203, 205, 207 and 209) reached $10^{10}$ CFU/mL when cultured in the original pH value of about 6.5. When the pH value was set to 3.2, the cell numbers of all the strains slightly decreased, and there was no statistically significant difference in the cell number between GKF3 and the other four strains. When the pH value of the culture medium decreased to pH 2.4, the cell numbers of ATCC 23271 (bar 203), BCRC 12190 (bar 207) and BCRC 10360 (bar 209) were significantly lower than that of GKF3 (bar 201, p<0.05), except for BCRC 12194 (bar 205). When the pH value of the culture medium decreased to pH 2.0, the cell numbers of ATCC 23271 (bar 203), BCRC 12190 (bar 205), BCRC 12194 (bar 207) and BCRC 10360 (bar 209) decreased to about $10^4$ CFU/mL and were significantly lower than that of GKF3 (bar 201, p<0.05), which remained its cell number to be $10^5$ CFU/mL. Accordingly, the viable cell number of GKF3 was significantly higher than that of other strains in an acidic environment, indicating that GKF3 had a better acid tolerance than that of the other strains, and thus GKF3 was more resistant to gastric acid when passing through the stomach.

TABLE 2

Cell Numbers of GKF3 and Other Strains in Acid Tolerance Test

| pH value | GKF3 | ATCC 23271 | BCRC 12190 | BCRC 12194 | BCRC 10360 |
|---|---|---|---|---|---|
| pH 6.5 | 10.0 ± 0.20 | 9.7 ± 0.30 | 9.9 ± 0.30 | 9.9 ± 0.41 | 10.0 ± 0.50 |
| pH 3.2 | 9.6 ± 0.59 | 9.5 ± 0.11 | 9.2 ± 0.20 | 9.8 ± 0.20 | 9.4 ± 0.30 |
| pH 2.4 | 7.9 ± 0.00 | 6.1 ± 0.22* | 7.1 ± 0.67 | 6.8 ± 0.34* | 5.3 ± 0.34* |
| pH 2.0 | 5.1 ± 0.15 | 3.1 ± 0.39# | 3.1 ± 0.31# | 4.2 ± 0.30# | 3.5 ± 0.20# |

Values were presented as mean ± standard deviation (SD) (n = 3) and the unit was log CFU/mL.
*represented a significant difference compared to GKF3 (pH 2.4; p < 0.05).
represented a significant difference compared to GKF3 (pH 2.0; p < 0.05).

Phenotypic Analysis—Bile Tolerance Test

GKF3, ATCC 23271, BCRC 12190, BCRC 12194 and BCRC 10360, were recovered. These strains were inoculated in an MRS liquid medium with 0.3% bile salt and cultured at 37° C. for half an hour, followed by serial dilution, spread plate, incubation and finally colony count. Experimental results were shown in TABLE 3 and FIG. 3.

Figure 3:
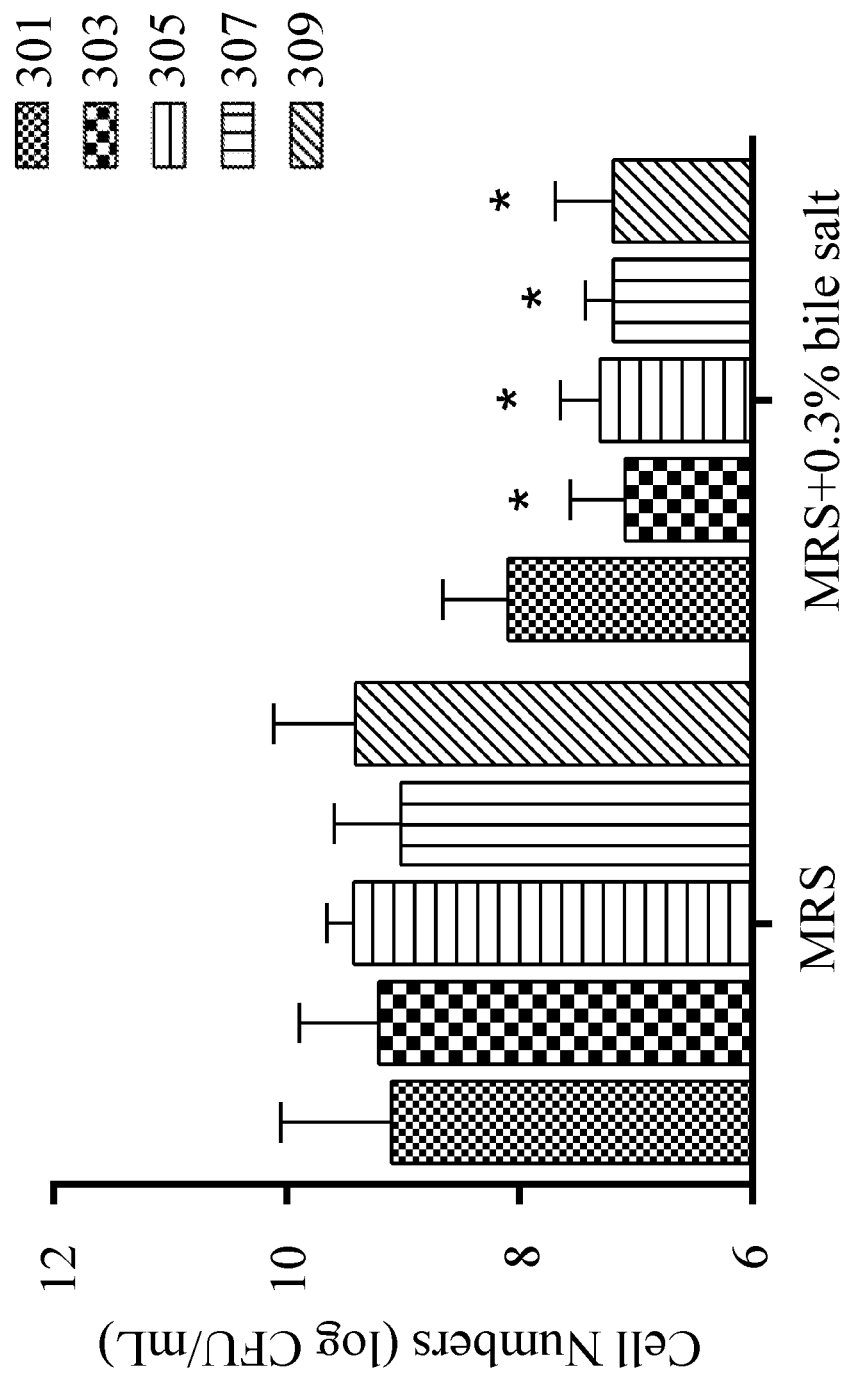
FIG. 3 shows the viable cell numbers of *Lactobacillus fermentum* GKF3 and other strains in the bile tolerance test.

FIG. 3 represented cell numbers of *L. fermentum* GKF3 and other strains in the bile tolerance test. The horizontal axis represented the medium content, and the vertical axis represented the cell numbers. The bars 301, 303, 305, 307 and 309 represented the GKF3, ATCC 23271, BCRC 12190, BCRC 12194 and BCRC 10360, respectively. The symbol "*" represented a significant difference in cell numbers between GKF3 and the other strains (p<0.05).

As shown in TABLE 3 and FIG. 3, the cell number of GKF3 (bar 301) and that of the other four strains (bars 303, 305, 307 and 309) reached $10^9$ CFU/mL when the culture took place in the original MRS liquid medium. In the MRS liquid medium with 0.3% bile salt, the cell numbers of all strains except GKF3 decreased to $10^7$ CFU/mL and were statistically lower than that of GKF3 (p<0.05). Accordingly, the viable cell number of the GKF3 was significantly higher than that of the other strains in an environment with a bile salt, indicating that the GKF3 had a better bile resistance than that of the other strains, and thus the GKF3 had a better ability to endure bile salt when passing through the digestive tract.

TABLE 3

Cell Numbers of GKF3 and Other Strains in Bile Tolerance Test.

| Bile salt amount | GKF3 | ATCC 23271 | BCRC 12190 | BCRC 12194 | BCRC 10360 |
|---|---|---|---|---|---|
| MRS | 9.1 ± 0.95 | 9.2 ± 0.68 | 9.4 ± 0.23 | 9.0 ± 0.57 | 9.4 ± 0.70 |
| MRS + 0.3% bile salt | 8.1 ± 0.56 | 7.1 ± 0.47* | 7.3 ± 0.34* | 7.2 ± 0.24* | 7.2 ± 0.50* |

Values were presented as mean ± SD (n = 3) and the unit was log CFU/mL.
*represented a significant difference compared to the GKF3 (MRS + 0.3% bile salt, p < 0.05).

Phenotypic Analysis—Heat Tolerance Test

GKF3 was compared with other strains in the heat tolerance test after GKF3 and other four strains, ATCC 23271, BCRC 12190, BCRC 12194 and BCRC 10360, were recovered. These five strains were heated respectively at 70° C. for 5, 10 and 15 min in a water bath, followed by serial dilution, spread plate, incubation and finally colony count. Experimental results were shown in TABLE 4 and FIG. 4.

Figure 4:
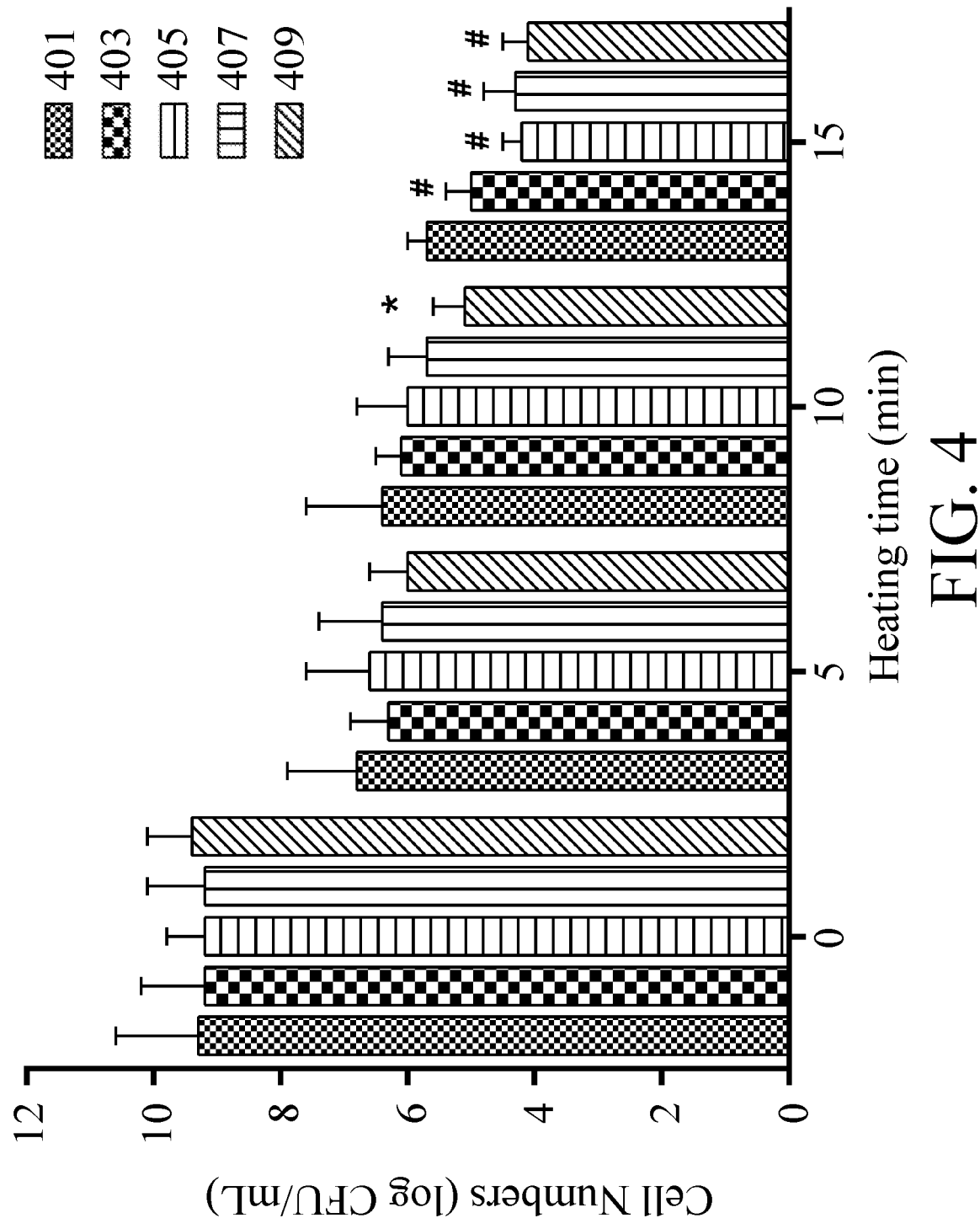
FIG. 4 shows the viable cell numbers of *Lactobacillus fermentum* GKF3 and other strains in the heat tolerance test.

FIG. 4 represented cell numbers of *L. fermentum* GKF3 and other strains in the heat tolerance test. The horizontal axis represented the time period of heating, and the vertical axis represented the cell numbers. The bars 401, 403, 405, 407 and 409 represented the GKF3, ATCC 23271, BCRC 12190, BCRC 12194 and BCRC 10360, respectively. The symbol "*" and "#" represented a significant difference in cell numbers between GKF3 and the other purchased strains heated for 10 min and 15 min, respectively (p<0.05).

As shown in TABLE 4 and FIG. 4, the cell numbers of the GKF3 and the other four strains reached $10^9$ CFU/mL without being heated (0 min). When heated at 70° C. for 5 min, the cell numbers of all the strains decreased to $10^6$ CFU/mL. When heated at 70° C. for 15 min, the cell numbers of ATCC 23271 (bar 403), BCRC 12190 (bar 405), BCRC 12194 (bar 407) and BCRC 10360 (bar 409) dramatically decreased to about $10^4$ CFU/mL and were significantly lower than that of the GKF3 (bar 401), which remained its cell numbers at $10^5$ CFU/mL (p<0.05). Accordingly, the viable cell number of the GKF3 was significantly higher than that of other strains in a high-temperature environment, indicating that the GKF3 has a better heat tolerance and better stability in the high-temperature environment.

TABLE 4

Cell Numbers of GKF3 and Other Strains in Heat Tolerance Test.

| Heating time | GKF3 | ATCC 23271 | BCRC 12190 | BCRC 12194 | BCRC 10360 |
|---|---|---|---|---|---|
| 0 | 9.3 ± 1.3 | 9.2 ± 1.0 | 9.2 ± 0.6 | 9.2 ± 0.9 | 9.4 ± 0.7 |
| 5 min | 6.8 ± 1.1 | 6.3 ± 0.6 | 6.6 ± 1.0 | 6.4 ± 1.0 | 6.0 ± 0.6 |
| 10 min | 6.4 ± 1.2 | 6.1 ± 0.4 | 6.0 ± 0.8 | 5.7 ± 0.6 | 5.1 ± 0.5* |
| 15 min | 5.7 ± 0.3 | 5.0 ± 0.4# | 4.2 ± 0.3# | 4.3 ± 0.5# | 4.1 ± 0.4# |

Values were presented as mean ± SD (n = 3) and the unit was log CFU/mL.
*represented a significant difference compared to the GKF3 (10 min) (p < 0.05).
represented a significant difference compared to the GKF3 (15 min) (p < 0.05)

Strain Culture

An isolated colony of the aforementioned *L. fermentum* GKF3 was inoculated into a liquid culture medium to perform a liquid culture. In a preferred embodiment, the liquid culture was performed under a condition with a temperature of 25 to 40° C., ventilation of 0 to 1 vvm of $N_2$ or $CO_2$, and a rotational speed of 250 to 1000 rounds per minutes (rpm). In a preferred embodiment, the time period for the liquid culture was 16 to 24 hours, but best for 18 hours, at which viable cell numbers reached the highest point. In a preferred embodiment, the liquid culture medium was the MRS liquid culture medium. In a preferred embodiment, a formula of the liquid culture medium was shown in TABLE 5. Then, the mass production of GKF3 was performed to obtain a whole fermented liquid.

TABLE 5

| Ingredient | Ratio (weight percentage) |
|---|---|
| Glucose | 1.00 to 10.00% |
| Yeast extract | 0.10 to 5.00% |
| Peptone | 0.10 to 5.00% |
| Micronutritions | 0.01 to 2.00% |
| Cysteine | 0.01 to 0.10% |
| Tween-80 | 0.05 o 1.00% |

Preparation of Lyophilized Powder

After the *L. fermentum* GKF3 underwent the mass production, the whole fermented liquid was collected and centrifuged to obtain pellets. In a preferred embodiment, 15 weight % (wt %) skim milk powder was added into the whole fermented liquid and incubated for 1 to 4 hours, so that the bacteria gathered into clots to increase the recovery rate, followed by centrifuging at a rotational speed of 1000 to 15000 rpm. The obtained pellet was mixed with a protection agent (6 wt % to 50 wt % skim milk powder) and lyophilized to obtain a lyophilized powder. Finally, the lyophilized powder was placed in the cold room for cryopreservation. In a preferred embodiment, the temperature and the time period for the lyophilization was programmed in gradients, in which the pellet was lyophilized first at 0° C. to −20° C. for 1 to 4 hours, −15° C. to −40° C. for the next 4 to 8 hours, and then frozen under −196° C. to −40° C. for more than 8 hours. In a preferred embodiment, the pellet was lyophilized under −5° C. for 2 hours, followed by −20° C. for 6 hours, and then the pellet is frozen under −50° C. for 16 hours. In a preferred embodiment, a temperature for the cryopreservation was −30° C. to 0° C. The lyophilized powder was then used as a test sample for animal administration for the following animal experiments. The dosage forms of the *L. fermentum* GKF3 in use of this invention could include but be not limited to the aforementioned lyophilized powder, the aforementioned whole fermented liquid including the bacteria and the liquid culture medium, as well as the pellet obtained by centrifuging the whole fermented liquid.

Experimental Animal 30 male ICR mice weighed about 20 g to 25 g per mice, were purchased from BioLASCO, Nangang District, Taipei, Taiwan. The mice were kept in regular cages having a stable environment of 23±2° C. room temperature, 50±5% humidity and a 12:12 light/dark cycle. The mice were given ad libitum accesses to feed and sterilized reverse osmosis water. All the process of the animal experiment was reviewed and approved by the regulation of Institutional Animal Care and Use Committee (IACUC) of Hung Kuang University, Taiwan.

Feed and distilled drinking water were given to the experimental animals for a week to allow them to acclimatize in the laboratory environment. Then, the experimental animals were randomly grouped into five groups, a control group and four experimental groups A to D, with six mice each.

Experimental Design

The four different strains used for the experimental groups A to D were listed in TABLE 6. The four LAB mixed with saline solutions were orally administered to the mice once per day for four weeks while an equal volume of 0.9% saline was fed to the control group. This route of administration is carried out using a stainless steel-made feeding needle, which was usually soaked in the 75% ethanol solution, was rinsed and washed with the 0.9% saline before use.

TABLE 6

| Group | Feeding sample |
| --- | --- |
| Control | None |
| Experimental Group A | *Lactobacillus plantarum* (BCRC 910787; CGMCC 14565) |
| Experimental Group B | *Lactobacillus fermentum* (ATCC 23271) |
| Experimental Group C | *Lactobacillus fermentum* GKF3 (BCRC 910824; CGMCC 15203) |
| Experimental Group D | *Lactobacillus acidophilus* (BCRC 14064; ATCC 314) |

Before administration, all the mice were weighed once a week to calculate the average weights for each group. The daily oral administration dosage was calculated based on the body surface area, in which the conversion factor of a human adult to a mouse is 12.3. Therefore, the daily oral administration dosage for the mouse (body weight 25 g for a mouse) was converted from the daily dosage (1000 mg, equivalent to about $10^{11}$ viable bacteria) of a human adult (body weight 60 kg) according to the formula (I) listed below:

The daily oral administration dosage of the test sample for a mouse (g)={Daily dosage for a human adult/60 kg (the weight of a human adult)}×weight of a mouse (kg)×12.3 (the conversion factor of a human adult a mouse)  (I)

According to the aforementioned formula (I), the daily oral administration dosage for the experimental groups was 205 mg/kg, equivalent to 5.125 mg for a 25 g mouse.

The mice from each experimental group were restrained for 14 days to induce psychataxia prior to the initiation of any procedures. The mice were restrained in a transparent restrainer (100×40 mm) for two hours per day. After the four week period, the mice were anesthetized and then sacrificed. The blood samples were collected in ethylenediaminetetraacetic acid (EDTA) tubes, centrifuged at 4° C. and preserved at −80° C. The total hippocampi of the mice were removed immediately, homogenized in a cold saline solution and centrifuged at 4° C. for 10 min (13000×g). The supernatant was collected and preserved at −80° C. for subsequent biochemical evaluation.

Determination of Dopamine Levels

Usually, mice with low levels of dopamine and/or serotonin would have symptoms such as insomnia, dysautonomia, reduced focus, depression, i.e., having psychataxia. Therefore, the dopamine level in the brain was analyzed by a commercially available ELISA kit (Novus Biologicals, Littleton Colo., USA).

Figure 5:
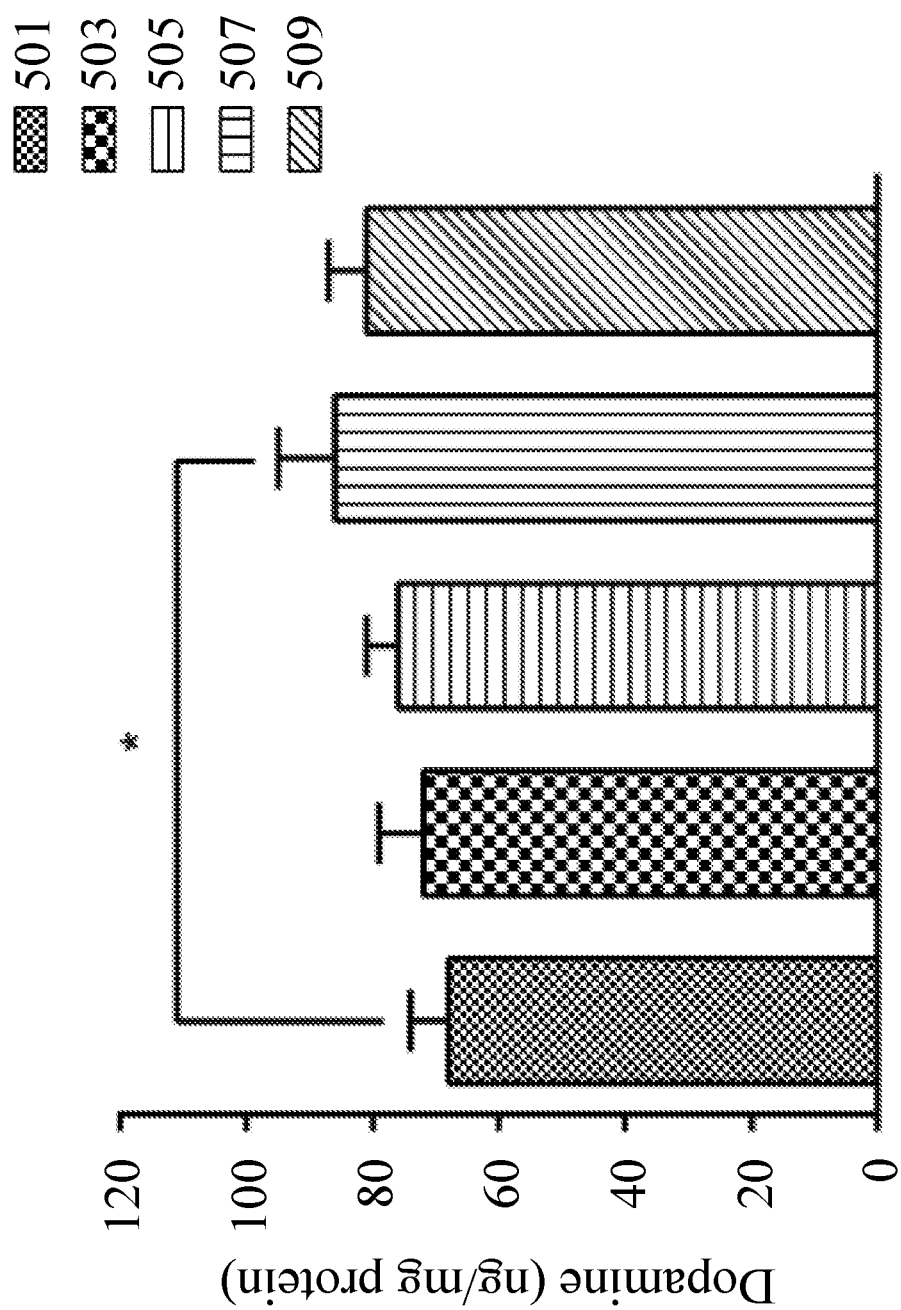
FIG. 5 shows the dopamine levels in the brain tissues of the mice.

The dopamine levels in the brain tissues of the mice for each group were shown in FIG. 5. FIG. 5 showed the dopamine levels in the brain tissues of the mice, in which the vertical axis represented the dopamine level, and the bars 501, 503, 505, 507 and 509 represented the control group, the experimental groups A, B, C and D, respectively. The symbol "*" represented a significant difference. The dopamine levels of the mice that were restrained to induce psychataxia were significantly lower. The mice administered with the *L. fermentum* GKF3 (the experimental group C) during the experiment process had significantly higher dopamine levels in the brain tissues compared to that of the control group (p<0.05). Compared to the other LAB strains, e.g., *L. plantarum* (BCRC 910787), *L. fermentum* (ATCC 23271) and *L. acidophilus* (BCRC 14064), *L. fermentum* GKF3 had a more statistically significant effect on dopamine release.

Determination of Serotonin Level

Figure 6:
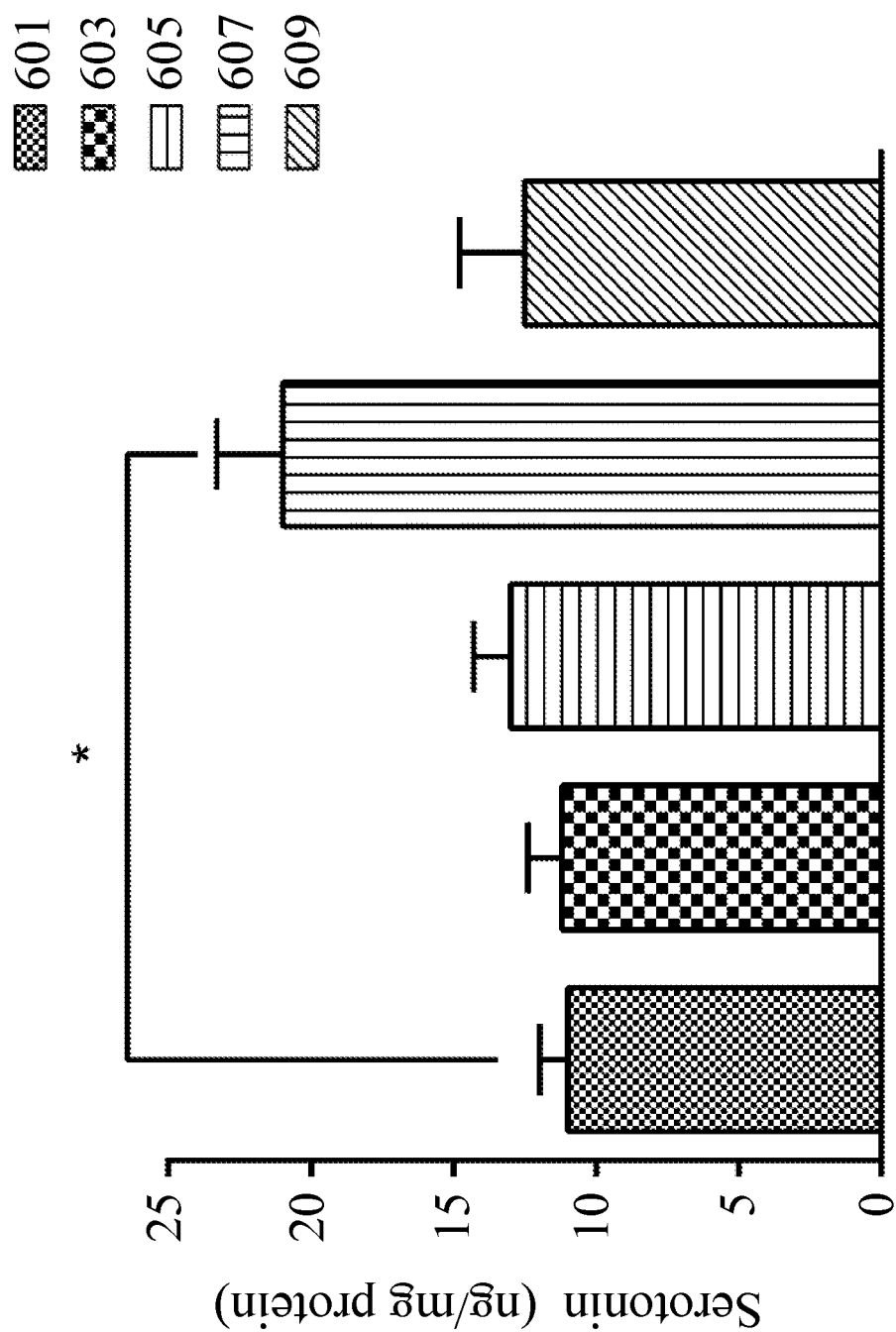
FIG. 6 shows the serotonin levels in the brain tissues of the mice.

A serotonin (5-HT) level in the brain was analyzed by a commercially available ELISA kit (Novus Biologicals, Littleton Colo., USA). The serotonin levels in the brain tissues of the mice for each group were shown in FIG. 6. FIG. 6 showed the serotonin levels in the brain tissues of the mice, in which the vertical axis represented the serotonin levels, and the bars 601, 603, 605, 607 and 609 represented the control group and the experimental groups A, B, C and D, respectively. The symbol "*" represented a significant difference. The serotonin levels of the mice that were restrained to induce psychataxia were significantly lower. The mice administered with the *L. fermentum* GKF3 (experimental group C) during the experiment process had significantly higher serotonin levels in the brain tissues compared to that of the control group (p<0.05). Compared to other LAB strains, e.g., *L. plantarum* (BCRC 910787), *L. fermentum* (ATCC 23271) and *L. acidophilus* (BCRC 14064), *L. fermentum* GKF3 had a more statistically significant effect on serotonin release.

Statistical Data Analysis

The experimental results were showed as means±SD and analyzed with commercially available analysis software, SPSS (the 12th edition). The differences were compared in the mean values between each group by one-way analysis of variance (ANOVA), followed by Duncan's multiple comparisons for post hoc tests. p<0.05 was considered statistical significance.

To sum up, the *L. fermentum* GKF3 was able to effectively increase the dopamine level and the serotonin level in the brain tissues of the mice that were restrained to induce psychataxia and thus decreased the occurrence risk of the psychataxia resulted from stress.

The present invention provides a composition including *Lactobacillus fermentum* GKF3, in which the composition has the effect to improve psychataxia.

Optionally, the composition can further include an additive. In a preferred embodiment, the additive can be an excipient, a preservative, a diluent, filler, an absorbefacient and a sweetener and the combination thereof. The excipient can be essentially selected from citric acid, calcium carbonate, tricalcium diphosphate, sucrose, or any combination of the above. The preservative can extend the shelf life of the composition, such as benzyl alcohol and parabens. The diluent can be essentially selected from a group consisting of water, ethyl alcohol, propylene glycol, glycerol, or any combination of the above. The filler can be essentially selected from a group consisting of lactose, galactose, high molecular weight polyethylene glycol or any combination of the above. The absorbefacient can be essentially selected from dimethyl sulfoxide (DMSO), azone, propylene glycol, glycerol and any combination of the above. The sweetener can be essentially selected from Acesulfame K, aspartame, saccharin, sucralose, neotame or any combination of the above. Except for the additives listed above, other proper additives can be selected under the premise that the medical effects of the active substance of lactic acid bacteria are not affected.

The composition can be developed into different products based on market demand. In a preferred embodiment, the composition can be developed into a drug, a feed, a drink, a nutritional supplement, a dairy product, a food or health food.

The composition can be adapted to different forms based on the requirement of the subject. In a preferred embodiment, the form of the composition can be powder, a tablet, a pellet, a suppository, a microcapsule, an ampoule, a liquid or a spray.

The composition can be applied to animals or humans. Without affecting the function of the *Lactobacillus fermentum* GKF3, the composition of the LAB can be made in any drug form and applied to animals or humans in a preferred way based on the drug form.

Preparation of Composition

The following aspect of composition 1 was shown as an example when GKF3 is applied in the use of food.

Composition 1: The lyophilized powder of *Lactobacillus fermentum* GKF3 (20 weight %, or wt %) was mixed completely with the preservative benzyl alcohol (8 wt %), diluent glycerol (7 wt %) and pure water (65 wt %) before storing at 4° C. The aforementioned wt % denoted the weight ratio of each composite accounting in the total weight of the composition.

The following aspect of composition 2 was shown as an example when the *Lactobacillus fermentum* GKF3 was applied as a liquid for medical use.

Composition 2: The lyophilized powder of *Lactobacillus fermentum* GKF3 (20 wt %) are mixed completely with the preservative benzyl alcohol (8 wt %), diluent glycerol (7 wt %), excipient sucrose (10 wt %) and pure water (55 wt %) before storing at 4° C. The aforementioned wt % denoted the weight ratio of each composite accounting in the total weight of the composition.

What is claimed is:

1. A method of improving psychataxia in a subject comprising orally administering to said subject a composition comprising an effective dosage of *Lactobacillus fermentum*, wherein the *Lactobacillus fermentum* is *Lactobacillus fermentum* GKF3 that is deposited in China General Microbiological Culture Collection Center (CGMCC), Chinese Academy of Sciences, Beijing 100101, People's Republic of China, on Jan. 12, 2018 with the accession number CGMCC 15203.

2. The method of claim 1, wherein the composition increases the dopamine release in the brain tissues of the subject orally administered with the composition when compared to a corresponding subject not orally administered with the composition.

3. The method of claim 1, wherein the composition increases the serotonin release in the brain tissues of the subject orally administered with the composition when compared to a corresponding subject not orally administered with the composition.

4. The method of claim 1, wherein symptoms of the psychataxia comprise insomnia, dysautonomia, decreased focus, depression and combination thereof.

* * * * *

SEQUENCE LISTING

```
<160> NUMBER OF SEQ ID NOS: 3

<210> SEQ ID NO 1
<211> LENGTH: 20
<212> TYPE: DNA
<213> ORGANISM: Artificial Sequence
<220> FEATURE:
<223> OTHER INFORMATION: recN gene forward primer

<400> SEQUENCE: 1
atccaaggtc aaaatgagca                                                   20

<210> SEQ ID NO 2
<211> LENGTH: 20
<212> TYPE: DNA
<213> ORGANISM: Artificial Sequence
<220> FEATURE:
<223> OTHER INFORMATION: recN gene reverse primer

<400> SEQUENCE: 2
cttcaacccg ttggttagtg                                                   20

<210> SEQ ID NO 3
<211> LENGTH: 1071
<212> TYPE: DNA
<213> ORGANISM: Lactobacillus fermentum GKF3

<400> SEQUENCE: 3
taacgctaag gttcagcccc tactagcgtc gtaccaagag cagtaccaag agtaccggcg        60
tttggaggcg gcggttaacc aaaagaaggc caacgagcaa cagtgggccc agcgcctcga       120
catgttgcgc taccaagtta aagaaattgg tgacgccgac ttgcgggccg acgaagaaga       180
tgaattaatc gccgaacgtg agcgactgga acacttccaa cagattgcca ccaccctcca       240
gcaggtggtt ggggtgttga acgatgacga agaggcgcct gtcttagacc aggtcgccac       300
```

```
catcatgaat gcagcccaag agattgcgcc cttcgatccc gaatacgatg acctggccca    360
gtccctttct gacgcctact attcactgca agacgtttcc aaccaagctg gccaccagtt    420
ggatagcctc gagtttgatg aggagcgact ggccacgatc aacgcccgct tagcgacgat    480
tgccgacttg gagcacaagt atggtgaaag cttagccgac gttttggcgt actacgacca    540
gatcaaagaa gagcttaccg atatggaggc cgcggccgat tcaggttccg atttggaaga    600
gcggttaaat gcggtccagg ccgatttgtt aaaccaaggg aacgccctga gccaagtgcg    660
gcaaacggcg gcccgcaaat tagccaagca ggttcacacc caactaaagg aactgtacat    720
ggataaggcg gtttttgaag tgaactttgc caaaaccaag aagccggtct tctctgccac    780
cgggatcgat caggttgaat tctacattca aaccaatcct ggtgaggcaa tgggaccctt    840
ggcccggatc gcctccgggg gggaactttc ccgggtgatg ctggccttaa agacgatctt    900
tgcccagggc gaaggggtta caagcatcat ctttgacgaa gtcgatactg gggtttccgg    960
gcgggtcgcc caagccattg ccgataagat tcgcttgatt gccgagggct cacaggtcct   1020
ttgcattact cacttaccac aggtggcagc ggttgcccaa caccacctct t            1071
```